(12) United States Patent
Solingen

(10) Patent No.: US 6,723,109 B2
(45) Date of Patent: Apr. 20, 2004

(54) DEPLOYABLE SURGICAL CLAMP WITH DELIVERY/RETRIEVAL DEVICE AND ACTUATOR

(75) Inventor: Simon Solingen, Los Angeles, CA (US)

(73) Assignee: Karl Storz Endoscopy-America, Inc., Culver City, CA (US)

( * ) Notice: Subject to any disclaimer, the term of this patent is extended or adjusted under 35 U.S.C. 154(b) by 43 days.

(21) Appl. No.: 09/968,101

(22) Filed: Oct. 1, 2001

(65) Prior Publication Data

US 2002/0107533 A1 Aug. 8, 2002

Related U.S. Application Data

(60) Provisional application No. 60/266,930, filed on Feb. 7, 2001.

(51) Int. Cl.$^7$ ................................. A61B 17/08
(52) U.S. Cl. ............... 606/151; 606/157; 606/142
(58) Field of Search ................... 606/151, 139, 606/142, 143, 120, 157, 158; 81/327, 518; 600/213

(56) References Cited

U.S. PATENT DOCUMENTS

| | | | |
|---|---|---|---|
| 3,506,012 A | * | 4/1970 | Brown .................... 606/142 |
| 4,038,987 A | * | 8/1977 | Komiya .................. 606/142 |
| 4,651,737 A | | 3/1987 | Deniega |
| 4,706,668 A | | 11/1987 | Backer .................... 128/325 |
| 4,957,500 A | | 9/1990 | Liang ...................... 606/157 |
| 5,766,189 A | * | 6/1998 | Matsuno .................. 606/158 |
| 5,855,590 A | | 1/1999 | Malecki et al. |
| 5,921,996 A | | 7/1999 | Sherman |
| 6,146,394 A | | 11/2000 | Morejohn et al. |
| 6,210,418 B1 | | 4/2001 | Storz et al. ............... 606/142 |
| 2001/0049540 A1 | | 12/2001 | Santilli |

FOREIGN PATENT DOCUMENTS

EP  02 00 2777  4/2002

* cited by examiner

Primary Examiner—Julian W. Woo
(74) Attorney, Agent, or Firm—St. Onge Steward Johnston & Reens LLC

(57) ABSTRACT

A surgical clamp system including a clamp, a delivery/retrieval device, and an actuator is provided. The clamp includes a pair of jaws actuatable relative to each other from a fully open to a fully closed position. The delivery/retrieval device is detachably connected to the clamp, and is operable by a surgeon to deploy the clamp, retrieve the clamp, or both. The actuator cooperates with the delivery/retrieval device and engages the clamp, and is operable by the surgeon to open and close the jaws of the clamp. The delivery/retrieval device and the actuator are operable to securely lock the jaws of the clamp in any position between the fully open and the fully closed positions, both during and after being detached from the delivery/retrieval device.

29 Claims, 5 Drawing Sheets

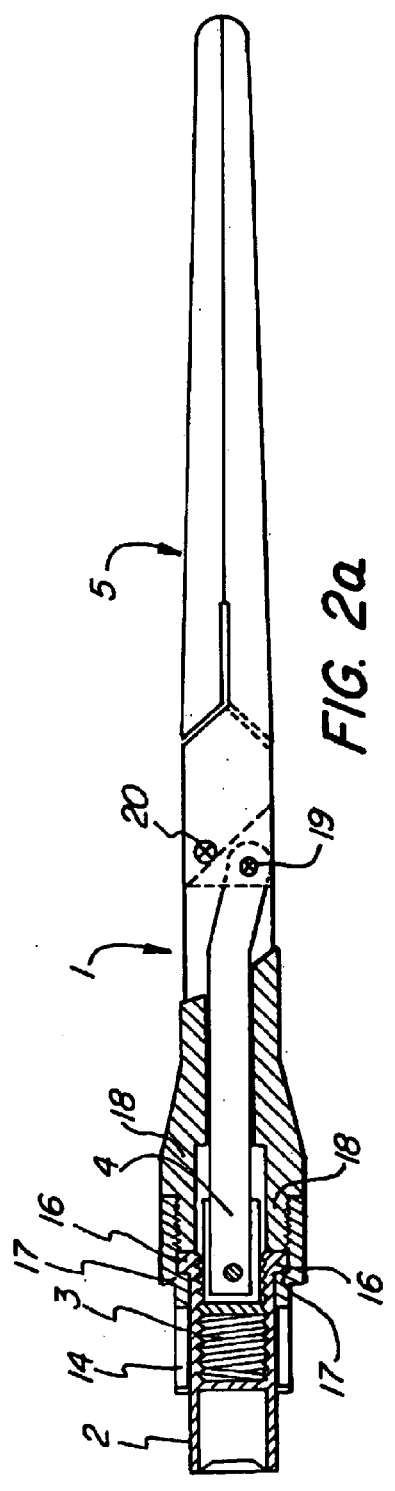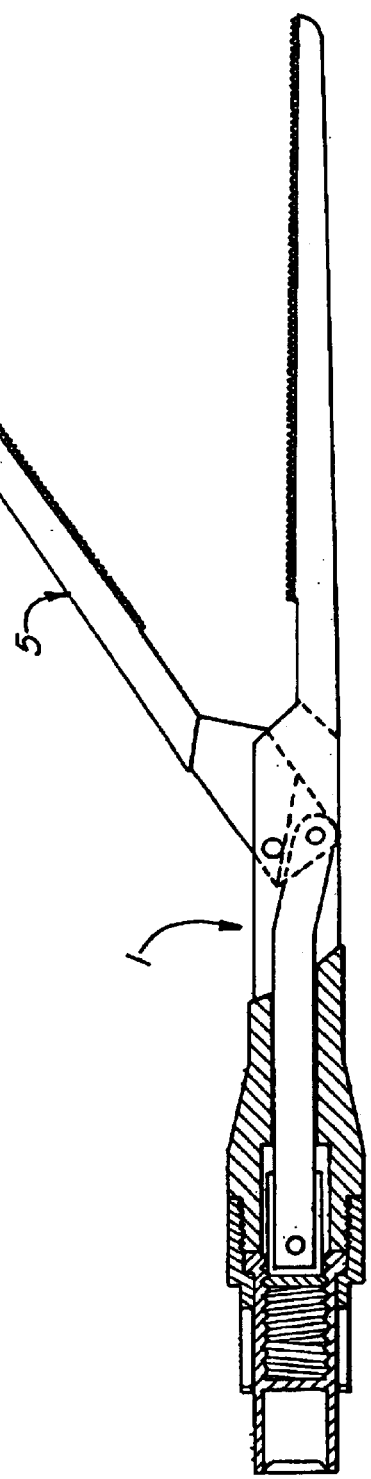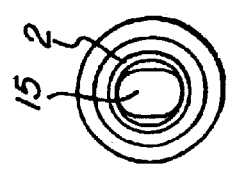

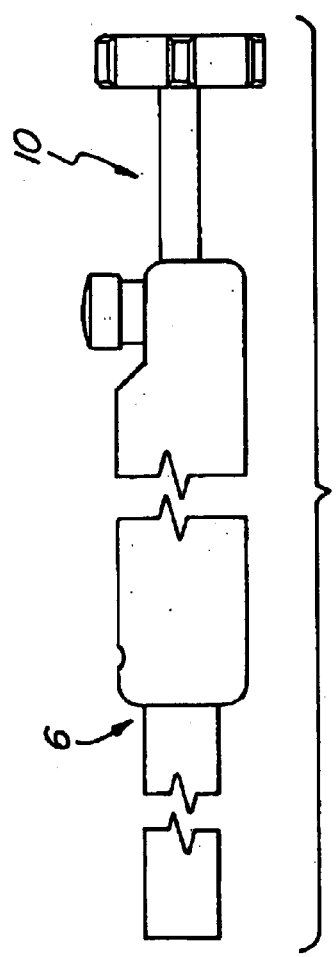
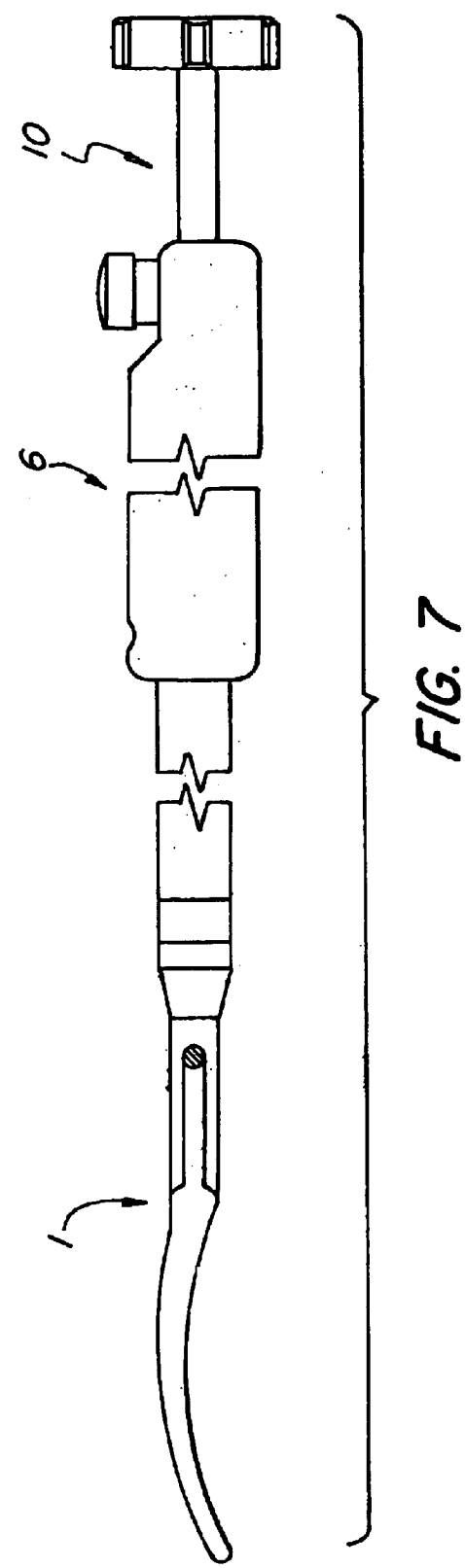

DEPLOYABLE SURGICAL CLAMP WITH DELIVERY/RETRIEVAL DEVICE AND ACTUATOR

CROSS-REFERENCE TO RELATED APPLICATIONS

The present application claims the benefit, under 35 U.S.C. 119(e), of Provisional Patent Application No. 60/266,930, filed Feb. 7, 2001.

FIELD OF THE INVENTION

The present invention relates to surgical clamping or grasping instruments for endoscopic or open surgery.

BACKGROUND OF THE INVENTION

Surgical clamps that can be detached from their dedicated actuators have been available for some time. These clamps are typically spring loaded, i.e. they depend upon the force of an integral spring to remain closed, and are opened by "squeezing" the proximal end of the jaw assemblies (Refer to Prior Art, FIG. 1a and FIG. 1b). Clamp delivery devices consist primarily of dedicated "pliers type" actuators that squeeze the clamp open, place the clamp at the desired location, and then release the clamp which then closes under integral spring pressure.

During certain surgical procedures, it may be necessary to temporarily and securely occlude body conduits (such as blood vessels and the like) of relatively large size, which due to disease, may have uneven wall thickness, or may be partially obstructed or stenotic. In open surgery, when access to the site is not limited, standard vascular type clamps (utilizing ring handles) are typically applied. Clamping force is increased until the body conduits are effectively and securely occluded, and then locked by means of ratchets. In endoscopic surgery, clamps are typically introduced to the surgery site through access ports (small openings made by a surgeon, and/or through natural existing body openings). However, it is desirable to reduce the number of openings made by the surgeon, as well as to reduce instrument clutter at the surgical site itself. Standard vascular type clamps do not lend themselves to reducing the number of surgical access ports and/or reducing instrument clutter at a surgical site. Spring loaded clamps have the limitation of not delivering sufficient clamping force to overcome the non-uniform thickness of body conduit walls to provide effective occlusion. Additionally, spring loaded clamps have a tendency of dislodging (slipping off) when disturbed, due to insufficient clamping force, thus risking patient safety. The tendency of dislodging (slipping off) applies, as well, when clamps are used to temporarily retract tissue.

The jaws of spring-loaded clamps are normally fully closed (exacting full clamping force as provided by spring tension) when detached from their delivery device, thus the clamping force cannot be varied by the surgeon. In order to apply differing clamping forces necessary for diverse medical procedures, many clamps with identical jaws and different spring tension must be available and used. One variable related to clamp effectiveness is tissue thickness (the thicker the tissue, the greater the resulting clamping force). Clamping force is limited by the spring tension, which is derived from the spring's physical size. If the spring physical size is large to provide greater clamping force, other aspects of surgery must be considered. Access ports typically have small diameters (the overall philosophy of endoscopic surgery is to make as few access port openings as possible, with the smallest diameter as possible), thus the larger sized springs required for greater clamping force are difficult to pass through the access port(s) to the surgical site. Additionally, the ability of the delivery method to squeeze the clamp open is limited; the greater spring tension required, the more difficult it becomes to remotely open the clamp.

What is desired, therefore, is a surgical clamp which delivers sufficient clamping force to overcome the non-uniform thickness of body conduit walls to provide effective occlusion, which does not have a tendency of dislodging (slipping off) when disturbed, which allows the clamping force to be varied by the surgeon, and which provides a clamping force which is not limited by spring tension.

SUMMARY OF THE INVENTION

Accordingly, it is an object of the present invention to provide a surgical clamp which delivers sufficient clamping force to overcome the non-uniform thickness of body conduit walls to provide effective occlusion.

Another object of the present invention is to provide a surgical clamp having the above characteristics and which does not have a tendency of dislodging (slipping off) when disturbed.

A further object of the present invention is to provide a surgical clamp having the above characteristics and which allows the clamping force to be varied by the surgeon.

Still another object of the present invention is to provide a surgical clamp having the above characteristics and which provides a clamping force which is not limited by spring tension.

These and other objects of the present invention are achieved by provision of a surgical clamp system including a clamp, a delivery/retrieval device, and an actuator. The clamp includes a pair of jaws actuatable relative to each other from a fully open to a fully closed position. The delivery/retrieval device is detachably connected to the clamp, and is operable by a surgeon to deploy the clamp, retrieve the clamp, or both. The actuator cooperates with the delivery/retrieval device and engages the clamp, and is operable by the surgeon to open and close the jaws of the clamp. The delivery/retrieval device and the actuator are operable to securely lock the jaws of the clamp in any position between the fully open and the fully closed positions, both during and after being detached from the delivery/retrieval device.

The pair of jaws of the clamp may be configured such that both are movable, or such that one is movable and the other is stationary. In one embodiment, the pair of jaws of the clamp may be substantially parallel to each other in any position between the fully open and the fully closed positions.

In one particular embodiment, the clamp includes a push-pull rod connected at one end to at least one of the pair of jaws of the clamp, a threaded screw connected to an end of the push-pull rod opposite to the end connected to the jaw or jaws, and a threaded nut engaging the screw, the nut being rotatable with respect to the screw in order to cause axial displacement of the screw and actuation of the pair of jaws. The nut is externally engageable by the actuator. In this embodiment, the jaws of the clamp are securely locked in any position between the fully open and the fully closed positions, both during and after being detached from the delivery/retrieval device by cooperation of the screw and the nut. It should be understood that while a screw/nut drive is described in the detailed example presented herein, other configurations for actuating and/or locking the jaws are also possible, such as a worm gear/drive gear arrangement, ratcheted push-pull rod, or the like.

In one particular embodiment, the delivery/retrieval device includes an elongated hollow shaft, a distal end of which is detachably connectable to the clamp, and a proximal end of which is adapted to receive the actuator. Preferably, the delivery/retrieval device is detachably connectable to the clamp by a bayonet connection.

In one particular embodiment, the actuator includes an elongated shaft having a distal end which rotatably engages the clamp in order to cause actuation of the pair of jaws of the clamp, and a proximal end having an externally accessible termination for permitting rotation of the shaft. Preferably, the distal end of the shaft rotatably engages the nut of the clamp.

The invention and its particular features and advantages will become more apparent from the following detailed description considered with reference to the accompanying drawings.

BRIEF DESCRIPTION OF THE DRAWINGS

FIG. 2a is a side view, partially in section, of one embodiment of a deployable clamp in accordance with the present invention, shown with its jaw closed;

FIG. 2b is a side view, partially in section, of the deployable clamp of FIG. 2a, shown with its jaw opened;

FIG. 2c is an end view of the deployable clamp of FIG. 2a;

FIG. 3c is an end view of the deployable clamp of FIG. 3a;

FIG. 4b is an end view of the delivery/retrieval device of FIG. 4a;

FIG. 5b is an end view of the actuator of FIG. 5a;

FIG. 6 is a side view illustrating the actuator of FIG. 5a inserted into the proximal end of the delivery/retrieval device of FIG. 4a; and FIG. 7 is a side view illustrating the clamp of FIG. 2a attached to the delivery/retrieval device of FIG. 4a, with the actuator of FIG. 5a latched in place.

DETAILED DESCRIPTION OF THE INVENTION

Figure 1A:
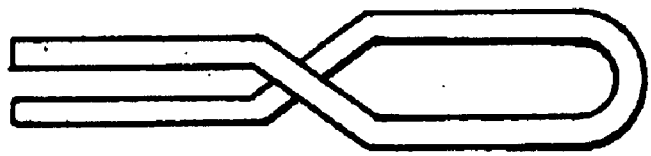
FIGS. 1a and 1b are side views of prior art surgical clamps that can be detached from their dedicated actuators.
Figure 1B:
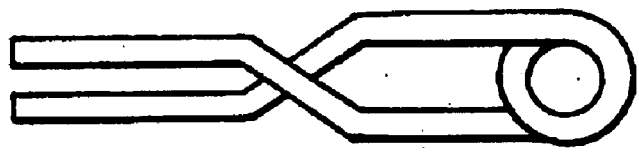

Referring first to FIGS. 2a and 2c, one embodiment of a deployable clamp 1 in accordance with the present invention is illustrated, shown with jaw 5 closed. FIG. 2b depicts the clamp 1 with jaw 5 open. Externally accessible nut 2 is threaded over screw 3 and prevented from axial displacement by flange 16 kept rotatably between bushing 17 and clamp body 18. Screw 3 is permanently coupled to push-pull rod 4, which is engaged to jaw 5 by means of articulation 19. Rotating nut 2 causes axial displacement of screw 3, which pulls or pushes on the jaw 5 by means of push-pull rod 4 acting over articulation 19, causing jaw 5 to articulate about pivot 20. It should be understood that while a screw/nut drive is described in the detailed example presented herein, the screw and nut can be interchanged (i.e. the nut can be attached to the push-pull rod), and that other configurations for actuating the jaws are also possible. For example, nut 2 could be replaced by a worm gear and screw 3 could be replaced with a rack gear which cooperates with the worm gear such that jaws are actuated by action of the gear system. In another arrangement, nut 2 can be replaced by a worm gear and the proximal end(s) of the movable jaw(s) be configured as a gear(s) sector(s) which cooperate(s) with the worm gear such that jaws are actuated by action of the gear system. In another arrangement, the push-pull rod could be configured as a ratchet rack and a pawl provided within the mechanism, in which case actuation of the jaws would be effected by axial displacement of an actuator. Other arrangements are also possible.

Figure 3A:
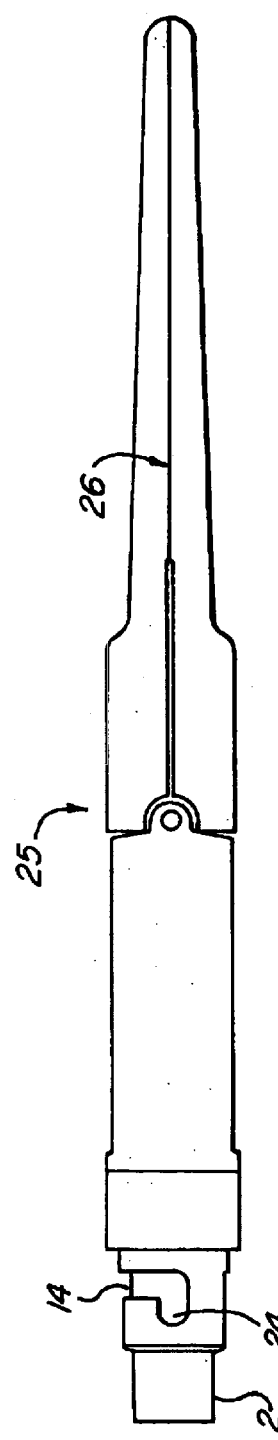
FIG. 3a is a side view of another embodiment of a deployable clamp in accordance with the present invention, shown with its jaw closed.
Figure 3B:
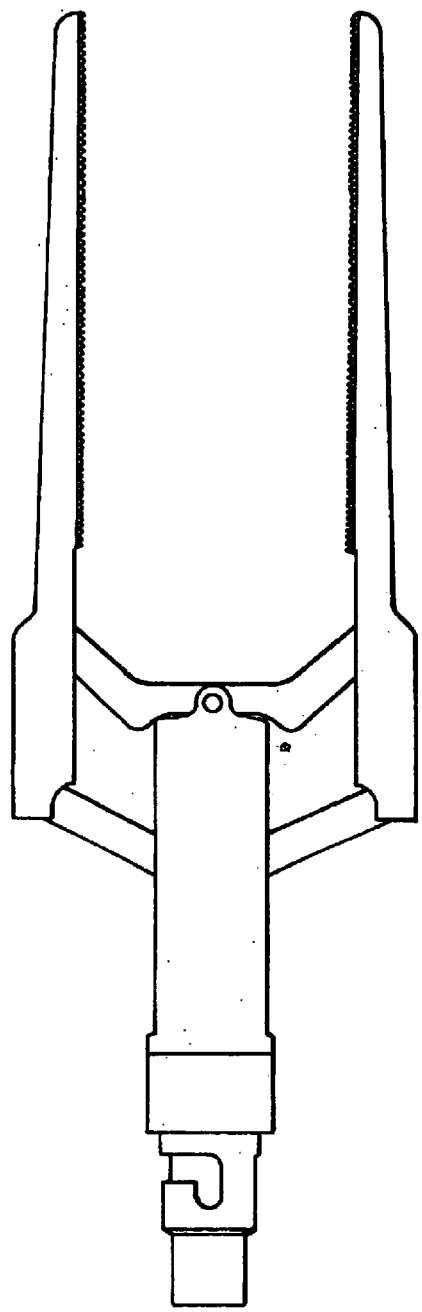
FIG. 3b is a side view of the deployable clamp of FIG. 3a, shown with its jaw opened.
Figure 3C:
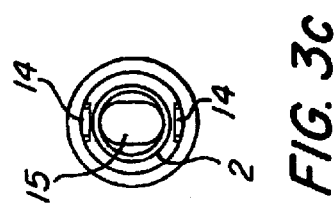

FIGS. 3a and 3c depict another embodiment of the deployable clamp 25, where two jaws are articulated and can open and close apposing (parallel to) each other 26. FIG. 3b depicts clamp 25 with both jaws open. The mechanism to open and close both jaws is identical to that described in FIG. 2a and 2b. Various jaw types (long, short, curved, etc.) can be utilized with the described clamping mechanism as required depending upon the surgical procedure being performed.

Figure 4A:
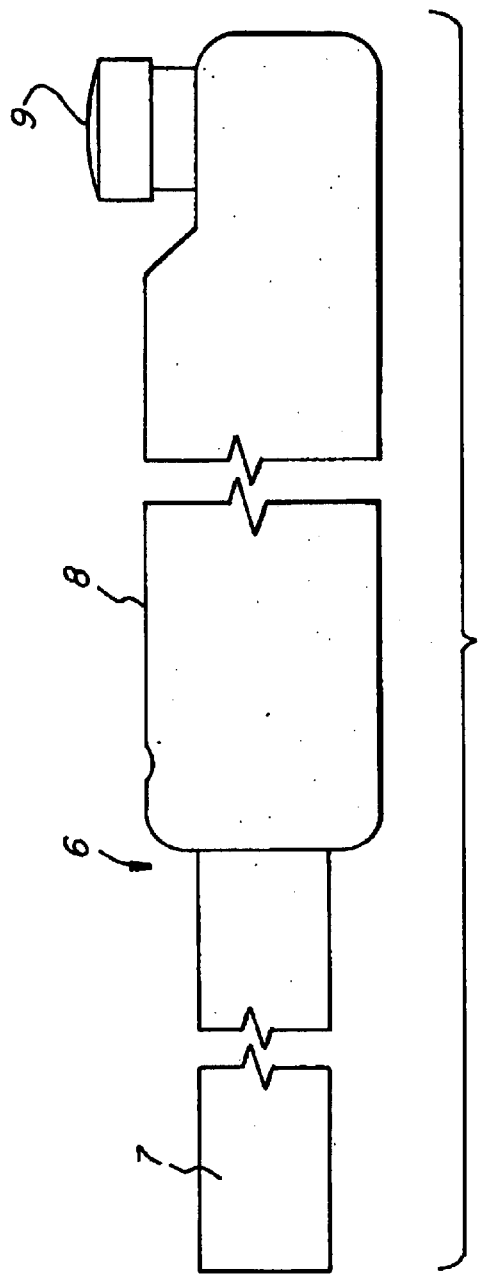
FIG. 4a is a side view of one embodiment of a delivery/retrieval device in accordance with the present invention.
Figure 4B:
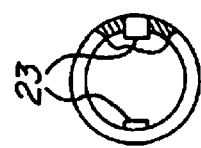

Referring now to FIGS. 4a and 4b, one embodiment of the delivery/retrieval device 6 is shown comprising a hollow shaft 7, handle 8, and a spring loaded latching mechanism (not shown) that can be released by push-button 9.

Figure 5A:
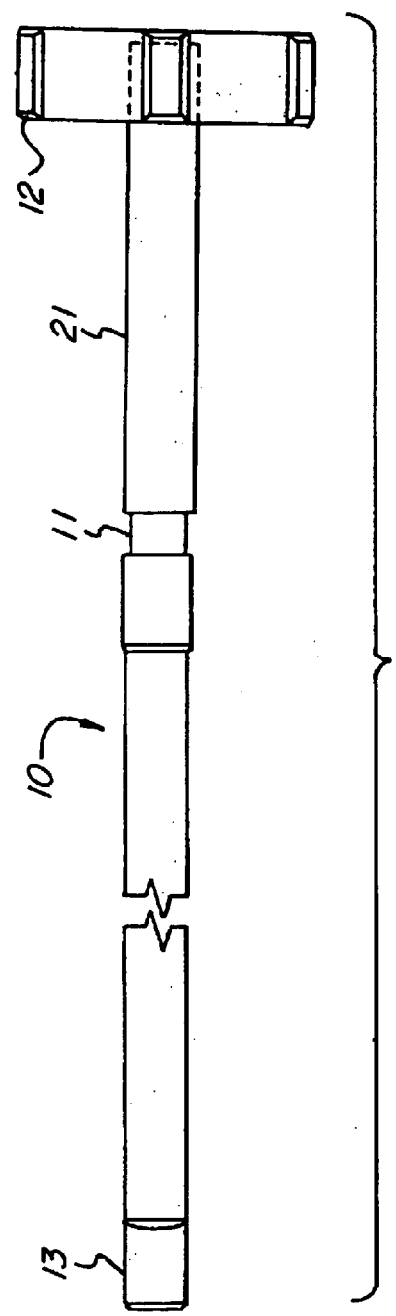
FIG. 5a is a side view of one embodiment of an actuator in accordance with the present invention.
Figure 5B:

FIGS. 5a and 5b depict one embodiment of an actuator 10 comprising a shaft 21 with proximal knob 12, and groove 11 which, when engaged by spring loaded latching mechanism (not shown), prevents shaft 21 from displacing axially. Distal end 13 of shaft 21 engages slot 15 (FIG. 2c) in nut 2 (FIG. 2c) of clamp 1 or clamp 25 (FIG. 3c).

FIG. 6 depicts actuator 10 inserted into the proximal end of delivery/retrieval device 6, while FIG. 7 depicts clamp 1 attached to delivery/retrieval device 6, with actuator 10 latched in place.

The following describes a typical use of either clamp 1 or clamp 25, delivery/retrieval device 6, and actuator 10.

The proximal end of clamp 1, 25 is inserted into distal end of hollow shaft 7 and rotated to engage and lock bayonet pins 23 inside distal end of hollow shaft 7 of delivery/retrieval device 6 to bayonet 14 (FIG. 2a and FIG. 3a). While holding handle 8, actuator 10 is introduced into the proximal end of handle 8, and pushed through and simultaneously rotated in hollow shaft 7 until distal end 13 penetrates and engages slot 15 of nut 2, at which point spring loaded latch mechanism (not shown) engages grove 11 and locks actuator 10 in place. Bayonet 14 is provided with axial grooves 24 (FIG. 3a) which are engaged to pins 23 (FIGS. 4a and 4b) when actuator 10 is locked in place thus pushing against the bottom of slot 15. Clamp 1 is prevented from rotating with respect to hollow shaft 7, which keeps the clamp securely locked place. Clamp 1 is prevented from being removed from hollow shaft 7 until latch (not shown) is disengaged from groove 11 and actuator 10 is withdrawn.

The assembled system is introduced into the surgical site, jaw 5 is opened by rotating knob 12, while holding handle 8 stationery. The open clamp is placed over the desired tissue, and jaw 5 is closed by rotating knob 12 in the opposite direction, while holding handle 8 stationery. Tactile feedback, representative of the delivered clamping force, is provided to the surgeon via the resistance to rotation felt on knob 12. Once the desired clamping force is achieved, push button 9 is pressed releasing actuator shaft 21. Actuator 10 can then be removed from delivery/retrieval device 6.

Delivery/retrieval device 6 is removed from deployed clamp 1 by use of a grasping means (i.e. a pair endoscopic hemostats or the like) to hold clamp 1 stationery, while handle 8 is rotated to disengage bayonet pins 23 from axial grooves 14. Delivery/retrieval device 6 can then be removed from the surgery site, as well as the employed grasping means used during clamp and delivery/retrieval device separation.

When deployed clamp 1 is no longer required, delivery/retrieval device 6 is reintroduced into the surgical site, and by use of a grasping means, clamp 1 is held stationery. Distal end of hollow shaft 7 is slipped over the proximal end of clamp 1 and handle 8 is simultaneously pushed and rotated to engage bayonet pins 23 with bayonet 14. While holding handle 8, actuator 10 in introduced into the proximal end of handle 8, and pushed through and simultaneously rotated in hollow shaft 7 until distal end 13 penetrates and engages slot 15 of nut 2, at which time latch (not shown) engages grove 11 and locks actuator 10 in place. Knob 12 is then rotated, while handle 8 is held stationery, to open jaw 5 of clamp 1. Once jaw 5 is open, clamp 1 is pulled away from the tissue. Knob 12 is rotated, while handle 8 is held stationery, until jaw 5 is fully closed, then the entire assembly can be withdrawn from the surgical site.

The present invention, therefore, provides a surgical clamp which delivers sufficient clamping force to overcome the non-uniform thickness of body conduit walls to provide effective occlusion, which does not have a tendency of dislodging (slipping off) when disturbed, which allows the clamping force to be varied by the surgeon, and which provides a clamping force which is not limited by spring tension.

Although the invention has been described with reference to a particular arrangement of parts, features and the like, these are not intended to exhaust all possible arrangements or features, and indeed many other modifications and variations will be ascertainable to those of skill in the art.

What is claimed is:

1. A surgical clamp system comprising:
   a clamp having a pair of jaws actuatable relative to each other from a fully open to a fully closed position;
   a delivery/retrieval device defining a longitudinal opening there-through, a distal portion of the opening configured to engage with said clamp, said delivery/retrieval device being operable by a surgeon to perform a function selected from the group comprising deploying said clamp, retrieving said clamp, or both;
   an actuator cooperating with said delivery/retrieval device, said actuator being at least partially insertable through the longitudinal opening of said delivery/retrieval device for engaging said clamp, said actuator being operable by the surgeon to open and close the jaws of said clamp; and
   wherein said delivery/retrieval device and said actuator are operable to securely lock the jaws of said clamp in any position between the fully open and the fully closed positions, said secured locking of the jaws of said clamp being maintained both before and after said clamp is detached from said delivery/retrieval device.

2. The surgical clamp system of claim 1 wherein both of the pair of jaws of said clamp are movable.

3. The surgical clamp system of claim 1 wherein one of the pair of jaws of said clamp is movable and the other of the pair of jaws of said clamp is stationary.

4. The surgical clamp system of claim 1 wherein the pair of jaws of said clamp is substantially parallel to each other in any position between the fully open and the fully closed positions.

5. The surgical clamp system of claim 1 wherein said clamp comprises:
   a push-pull rod connected at one end to at least one of the pair of jaws of said clamp;
   a threaded screw connected to an end of said push-pull rod opposite to the end connected to at least one of the pair of jaws of said clamp;
   a threaded nut engaging said screw, said nut being rotatable with respect to said screw in order to cause axial displacement of said screw and actuation of the jaw or pair of jaws; and
   wherein said nut is externally engageable by said actuator.

6. The surgical clamp system of claim 5 wherein the jaws of said clamp are securely locked in any position between the fully open and the fully closed positions, both during and after being detached from said delivery/retrieval device by cooperation of said screw and said nut.

7. The surgical clamp system of claim 5 wherein said actuator comprises elongated shaft having a distal end which rotatably engages said clamp in order to cause actuation of the jaw or pair of jaws of said clamp, and a proximal end having an externally accessible termination for permitting rotation of the shaft.

8. The surgical clamp system of claim 7 wherein the distal end of the shaft rotatably engages the nut of said clamp.

9. The surgical clamp system of claim 1 wherein said clamp comprises:
   a push-pull rod connected at one end to at least one of the pair of jaws of said clamp;
   a threaded nut connected to an end of said push-pull rod opposite to the end connected to at least one of the pair of jaws of said clamp;
   a threaded screw engaging said nut, said screw being rotatable with respect to said nut in order to cause axial displacement of said nut and actuation of the jaw or pair of jaws; and
   wherein said screw is externally engageable by said actuator.

10. The surgical clamp system of claim 9 wherein the jaws of said clamp are securely locked in any position between the fully open and the fully closed positions, y both during and after being detached from said delivery/retrieval device by cooperation of said screw and said nut.

11. The surgical clamp system of claim 1 wherein said clamp comprises:
    a push-pull rod connected at one end to at least one of the pair of jaws of said clamp;
    a rack gear connected to an end of said push-pull rod opposite to the end connected to at least one of the pair of jaws of said clamp;
    a worm gear engaging said rack gear, said worm gear being rotatable with respect to said rack gear in order to cause axial displacement of said rack gear and actuation of the jaw or pair of jaws; and
    wherein said worm gear is externally engageable by said actuator.

12. The surgical clamp system of claim 11 wherein the jaws of said clamp are securely locked in any position between the fully open and the fully closed positions, both during and after being detached from said delivery/retrieval device by cooperation of said rack gear and said worm gear.

13. The surgical clamp system of claim 1 wherein said delivery/retrieval device comprises an elongated hollow shaft, a distal end of which is detachably connectable to said clamp, and a proximal end of which is adapted to receive said actuator.

14. The surgical clamp system of claim 13 wherein said delivery/retrieval device is detachably connectable to said clamp by a bayonet connection.

15. The surgical clamp system of claim 1 wherein said actuator comprises an elongated shaft having a distal end which rotatably engages said clamp in order to cause actuation of the jaw or pair of jaws of said clamp, and a proximal end having an externally accessible termination for permitting rotation of the shaft.

16. The surgical clamp system of claim 1 wherein the pair of jaws of said clamp are only parallel to each other when fully closed, defining an angle when in any position other than fully closed.

17. The surgical clamp system of claim 1 wherein said clamp comprises:
 a push-pull rod connected at one end to at least one of the pair of jaws of said clamp, said push-pull rod provided with at least one ratchet tooth along its axis;
 a pawl being fixed with respect to the immobile/indifferent structure of said clamp, said pawl engaging said at least one ratchet tooth, and being capable of locking the push-pull rod in any position within its axial travel range;
 wherein said push-pull rod is externally engageable by said actuator.

18. The surgical clamp system of claim 17 wherein the jaws of said clamp are securely locked in any position between the fully open and the fully closed positions by engagement of said at least one ratchet tooth and said pawl, both during and after being detached from said delivery/retrieval device.

19. The surgical clamp system of claim 17 wherein said actuator comprises an elongated shaft having a distal end which axially engages said clamp in order to cause actuation of the jaw or pair of jaws of said clamp, and a proximal end having an externally accessible termination for permitting axial displacement of the shaft.

20. The surgical clamp system of claim 17 wherein both of the pair of jaws of said clamp is movable relative to each other.

21. The surgical clamp system of claim 17 wherein one of the pair of jaws of said clamp is movable and the other of the pair of jaws of said clamp is stationary.

22. The surgical clamp system of claim 1 wherein said clamp comprises:
 a worm gear which engages the proximal ends of the jaws, said proximal ends of the jaws configured as gear sectors containing at least one tooth each, said worm gear being rotatable and causing the actuation of said jaws; and
 wherein said worm gear is externally engageable by said actuator.

23. The surgical clamp system of claim 22 wherein both of the pair of jaws of said clamp is movable relative to each other.

24. The surgical clamp system of claim 22 wherein one of the pair of jaws of said clamp is movable and the other of the pair of jaws of said clamp is stationary.

25. A surgical clamp system comprising:
 a clamp having a pair of jaws actuatable relative to each other from a fully open to a fully closed position, said clamp further comprising a push-pull rod connected at one end to at least one of the pair of jaws, a threaded screw connected to an end of the push-pull rod opposite to the end connected to at least one of the pair of jaws, and a threaded nut engaging the screw, the nut being rotatable with respect to the screw in order to cause axial displacement of the screw and actuation of the pair of jaws;
 a delivery/retrieval device, said delivery/retrieval device comprising an elongated hollow shaft, a distal end of which is detachably connectable to said clamp, said delivery/retrieval device being operable by a surgeon to perform a function selected from the group comprising deploying said clamp, retrieving said clamp, or both;
 an actuator received through a proximal end of said delivery/retrieval device, said actuator comprising an elongated shaft having a distal end which rotatably engages the nut of said clamp and a proximal end having an externally accessible termination operable by the surgeon to open and close the jaws of said clamp; and
 wherein said delivery/retrieval device and said actuator are operable to securely lock the jaws of said clamp in any position between the fully open and the fully closed positions, said secured locking of the jaws of said clamp being maintained both before and after said clamp is detached from said delivery/retrieval device by cooperation of the screw and the nut of said clamp.

26. The surgical clamp system of claim 25 wherein both of the pair of jaws of said clamp are movable relative to each other.

27. The surgical clamp system of claim 25 wherein one of the pair of jaws of said clamp is movable and the other of the pair of jaws of said clamp is stationary.

28. The surgical clamp system of claim 25 wherein the pair of jaws of said clamp are substantially parallel to each other in any position between the fully open and the fully closed positions.

29. The surgical clamp system of claim 25 wherein said delivery/retrieval device is detachably connectable to said clamp by a bayonet connection.

* * * * *